United States Patent
Chen et al.

(10) Patent No.: US 10,696,638 B2
(45) Date of Patent: Jun. 30, 2020

(54) COMPOUNDS FOR INHIBITING AGC KINASE AND PHARMACEUTICAL COMPOSITIONS COMPRISING THE SAME

(71) Applicant: Industrial Technology Research Institute, Hsinchu (TW)

(72) Inventors: Chih-Hung Chen, Tainan (TW); Yi-Hsun Chen, Hsinchu (TW); Jui-Wen Huang, Zhubei (TW); Kuo-Kuei Huang, Zhubei (TW); Chih-Peng Liu, Hsinchu (TW); Chrong-Shiong Hwang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 16/206,000

(22) Filed: Nov. 30, 2018

(65) Prior Publication Data
US 2019/0194137 A1 Jun. 27, 2019

Related U.S. Application Data

(60) Provisional application No. 62/610,446, filed on Dec. 26, 2017.

(51) Int. Cl.
| | | |
|---|---|---|
| C07D 217/02 | (2006.01) | |
| A61K 31/472 | (2006.01) | |
| A61P 27/02 | (2006.01) | |
| A61K 31/4725 | (2006.01) | |
| A61K 9/08 | (2006.01) | |
| A61K 9/00 | (2006.01) | |

(52) U.S. Cl.
CPC .......... *C07D 217/02* (2013.01); *A61K 31/472* (2013.01); *A61K 31/4725* (2013.01); *A61P 27/02* (2018.01); *A61K 9/0048* (2013.01); *A61K 9/08* (2013.01)

(58) Field of Classification Search
CPC .................................................... C07D 217/02
USPC ......................................................... 546/143
See application file for complete search history.

(56) References Cited

U.S. PATENT DOCUMENTS

| | | | |
|---|---|---|---|
| 4,785,008 | A | 11/1988 | Coquelet et al. |
| 8,153,792 | B2 | 4/2012 | Moussy et al. |
| 8,278,335 | B2 | 10/2012 | Machacek et al. |
| 8,367,706 | B2 | 2/2013 | Altman et al. |
| 8,394,826 | B2 | 3/2013 | deLong et al. |
| 8,455,514 | B2 | 6/2013 | deLong et al. |
| 8,912,209 | B2 | 12/2014 | Leysen et al. |
| 9,713,613 | B2 | 7/2017 | Uesugi et al. |
| 2003/0158198 | A1 | 8/2003 | Lee et al. |
| 2005/0113576 | A1 | 5/2005 | Lee et al. |
| 2007/0173530 | A1* | 7/2007 | deLong ............... C07D 217/02 514/307 |
| 2008/0167340 | A1 | 7/2008 | deLong et al. |
| 2010/0041671 | A1 | 2/2010 | Nakajima et al. |
| 2013/0131059 | A1 | 5/2013 | Lampe et al. |
| 2013/0177655 | A1 | 7/2013 | Sugimoto et al. |

FOREIGN PATENT DOCUMENTS

| | | | |
|---|---|---|---|
| TW | 201134825 | A1 | 10/2011 |
| WO | WO 02/057233 | A1 | 7/2002 |
| WO | WO 03/062215 | A1 | 7/2003 |
| WO | 2003080578 | A1 * | 10/2003 |
| WO | WO 03/080578 | A1 | 10/2003 |
| WO | WO 2005/105069 | A1 | 11/2005 |
| WO | WO 2007/000240 | A1 | 1/2007 |
| WO | WO 2007/026920 | A2 | 3/2007 |
| WO | WO 2008/110846 | A2 | 9/2008 |

OTHER PUBLICATIONS

Wu et al., Bioorg. Med. Chem. Letters (2010), vol. 20(11), pp. 3235-3239.*
Chen et al. "Chroman-3-amides as potent Rho kinase inhibitors", Bioorganic & Medicinal Chemistry Letters, 18, (2008), p. 6406-6409.
Donegan et al. "Discovery of molecular therapeutics for glaucoma: Challenges, successes, and promising directions", J Med Chem., Feb. 11, 2016, 59, (3), p. 788-809.
(Continued)

*Primary Examiner* — Taofiq A Solola
(74) *Attorney, Agent, or Firm* — Birch, Stewart, Kolasch & Birch, LLP

(57) ABSTRACT

A compound of formula (I) or a pharmaceutically acceptable salt thereof is provided. In formula (I), Ar is indazole, 5-isoquinoline, 6-isoquinoline, or their N-oxide. X is —C(=Z)—, wherein Z is N—CN, NH, $NR_4$, $NCOR_4$, $NCONR_4R_5$, NCO-aryl, S, or O. Y and J are independently H, alkyl, aryl, aminoalkyl, —$NH_2$, —CN, —OH, —O-alkyl, —O-aryl, —COOH, —$COOR_4$, —$CONHR_4$, —$CONHCH_2$-aryl, —$CONR_4CH_2$-aryl, —$NHCOR_4$, halogen, halogened alkyl, -alkyl-$OR_4$, -alkyl-$ONO_2$, alkyl-$ONO_2$, —$OCOOR_4$, —O(C=O)-aryl, —$CHR_4OH$, —$CH_2OH$, —$CH_2O(C=O)$-aryl, —$CH_2O(C=O)$—$R_4$, —$CHR_4O(C=O)$-aryl, —$CHR_4O(C=O)$—$R_4$, unsaturated carboxylic ester, substituted alkynyl, —$NHSO_2R_4$, —$SO_2R_4$, —$SO_2NHR_4$, or —$SO_2NR_4R_5$, or Y and J bond together to form a carbocylic or aromatic ring, wherein $R_4$ and $R_5$ are independently H, substituted C1-C6 alkyl, substituted aryl, cycloalkyl, alkylaryl, -alkyl-$NR_6R_7$, —$S(O)_{0-2}$-(alkyl-$NR_6R_7$). $R_1$, $R_2$ and $R_3$ are H, C1-C6 alkyl, cycloalkyl, aryl, alkylaryl, alkylheteroaryl, alkylheterocycle, wherein any one thereof is optionally substituted with one or more of OH, $NO_2$, or $NR_8R_9$.

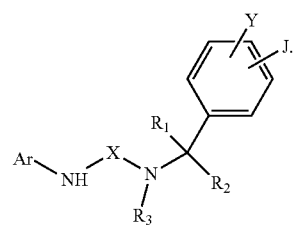

(I)

8 Claims, No Drawings

(56) References Cited

OTHER PUBLICATIONS

Feng et al. "Discovery of Substituted 4-(Pyrazol-4-yl)-phenylbenzodioxane-2-carboxamides as Potent and Highly Selective Rho Kinase (ROCK-II) Inhibitors", J. Med. Chem., 2008, 51, (21), p. 6642-6645.

Guan et al. "Advances in the studies of roles of Rho/Rho-kinase in diseases and the development of its inhibitors", European Journal of Medicinal Chemistry, 70, (2013), p. 613-622.

Henderson et al. "2,3-Diaminopyrazines as rho kinase inhibitors", Bioorganic & Medicinal Chemistry Letters, 20, (2010), p. 1137-1140.

Iwakubo et al. "Design and synthesis of Rho kinase inhibitors (II)", ScienceDirect, Bioorganic & Medicinal Chemistry, 15, (2007), p. 350-364.

Iwakubo et al. "Design and synthesis of rho kinase inhibitors (III)", ScienceDirect, Bioorganic & Medicinal Chemistry, 15, (2007), p. 1022-1033.

Morwick et al. "Hit to Lead Account of the Discovery of Bisbenzamide and Related Ureidobenzamide Inhibitors of Rho Kinase", J. Med. Chem., 2010, 53, p. 759-777.

Sehon et al. "Potent, Selective and Orally Bioavailable Dihydropyrimidine Inhibitors of Rho Kinase (ROCK1) as Potential Therapeutic Agents for Cardiovascular Diseases", J. Med. Chem., 2008, 51, p. 6631-6634.

Stavenger et al. "Discovery of Aminofurazan-azabenzimidazoles as Inhibitors of Rho-Kinase with High Kinase Selectivity and Antihypertensive Activity", J. Med. Chem., 2007, 50, p. 2-5.

Takami et al. "Design and synthesis of Rho kinase inhibitors (I)", ScienceDirect, Bioorganic & Medicinal Chemistry, 12, (2004), p. 2115-2137.

Extended European Search Report for European Application No. 18214556.5, dated Feb. 13, 2019.

LoGrasso et al., "Rho Kinase (ROCK) Inhibitors and Their Application to Inflammatory Disorders," Current Topics in Medicinal Chemistry, vol. 9, No. 8, 2009, pp. 704-723.

\* cited by examiner

COMPOUNDS FOR INHIBITING AGC KINASE AND PHARMACEUTICAL COMPOSITIONS COMPRISING THE SAME

CROSS REFERENCE TO RELATED APPLICATIONS

This application claims the benefit of U.S. Provisional Application No. 62/610,446, filed on Dec. 26, 2017, the entirety of which is incorporated by reference herein.

TECHNICAL FIELD

The disclosure relates to a compound for inhibiting AGC kinase or a pharmaceutically acceptable salt thereof, and a pharmaceutical composition comprising the same.

BACKGROUND

AGC kinase has become an attractive target for the treatment of many diseases such as hypertension, stroke, cancer and glaucoma.

Therefore, development of novel AGC kinase inhibitors with improved inhibitory activity is desired.

SUMMARY

In accordance with one embodiment of the disclosure, a compound of formula (I) or a pharmaceutically acceptable salt thereof is provided.

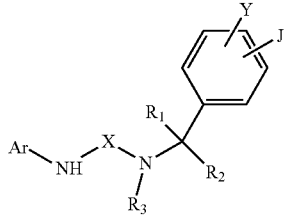

(I)

In formula (I), Ar is indazole, 5-isoquinoline, 6-isoquinoline, or their N-oxide, X is —C(=Z)—, wherein Z is N—CN, NH, $NR_4$, $NCOR_4$, $NCONR_4R_5$, NCO-aryl, S, or O, Y and J are independently H, $C_1$-$C_6$ alkyl, $C_6$-$C_8$ aryl, $C_1$-$C_6$ aminoalkyl, —$NH_2$, —CN, —OH, —O-alkyl, —O-aryl, —COOH, —$COOR_4$, —$CONHR_4$, —$CONHCH_2$-aryl, —$CONR_4CH_2$-aryl, —$NHCOR_4$, halogen, $C_1$-$C_6$ halogened alkyl, -alkyl-$OR_4$, -alkyl-$ONO_2$, —O-alkyl-$ONO_2$, —$OCOOR_4$, —O(C=O)-aryl, —$CHR_4OH$, —$CH_2OH$, —$CH_2O(C=O)$-aryl, —$CH_2O(C=O)$—$R_4$, —$CHR_4O$(C=O)-aryl, —$CHR_4O(C=O)$—$R_4$, unsaturated carboxylic ester, $C_2$-$C_{12}$ alkynyl, substituted $C_2$-$C_{12}$ alkynyl, —$NHSO_2R_4$, —$SR_4$, —$SO_2R_4$, —$SO_2NHR_4$, or —$SO_2NR_4R_5$, or Y and J bond together to form a carbocyclic or aromatic ring, wherein $R_4$ and $R_5$ are independently H, $C_1$-$C_6$ alkyl, $C_6$-$C_8$ aryl, substituted $C_1$-$C_6$ alkyl, substituted $C_6$-$C_8$ aryl, $C_5$-$C_{12}$ cycloalkyl, $C_7$-$C_{12}$ alkylaryl, -alkyl-$NR_6R_7$, -alkyl-$OR_6$, -alkyl-$ONO_2$, —$S(O)_{0-2}$-(alkyl-$NR_6R_7$), wherein $R_6$ and $R_7$ are independently H, alkyl, aryl or bond together with nitrogen atom to form a heterocyclic ring, and $R_1$, $R_2$ and $R_3$ are H, $C_1$-$C_6$ alkyl, cycloalkyl, aryl, alkylaryl, alkylheteroaryl, alkylheterocycle, wherein any one thereof is optionally substituted with one or more of OH, $ONO_2$, or $NR_8R_9$, wherein $R_8$ and $R_9$ are independently H, $C_1$-$C_6$ alkyl, $C_6$-$C_8$ aryl or bond together with nitrogen atom to form a heterocyclic ring.

In accordance with one embodiment of the disclosure, a pharmaceutical composition is provided. The pharmaceutical composition comprises an effective amount of the compound of formula (I) or a pharmaceutically acceptable salt thereof, and a pharmaceutically acceptable carrier.

A detailed description is given in the following embodiments.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

In the disclosure, molecular docking and three-dimensional quantitative structure-activity relationship are performed to design a new series of selective AGC inhibitors.

In the disclosure, a new series of selective AGC inhibitors based on, for example, pyridine, indazole or isoquinoline derivatives, is developed. An object of the present disclosure is to provide a preventing or treating agent for ophthalmic disorders. These compounds contain structural feature render them suitable for use in topical formulations. The structures described herein provide new compounds with therapeutically utility.

In accordance with one embodiment of the disclosure, a compound of formula (I) or a pharmaceutically acceptable salt thereof is provided.

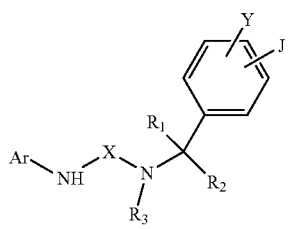

(I)

In formula (I), Ar is indazole, 5-isoquinoline, 6-isoquinoline, or their N-oxide, X is —C(=Z)—, wherein Z is N—CN, NH, $NR_4$, $NCOR_4$, $NCONR_4R_5$, NCO-aryl, S, or O, Y and J are independently H, $C_1$-$C_6$ alkyl, $C_6$-$C_8$ aryl, $C_1$-$C_6$ aminoalkyl, —$NH_2$, —CN, —OH, —O-alkyl, —O-aryl, —COOH, —$COOR_4$, —$CONHR_4$, —$CONHCH_2$-aryl, —$CONR_4CH_2$-aryl, —$NHCOR_4$, halogen, $C_1$-$C_6$ halogened alkyl, -alkyl-$OR_4$, -alkyl-$ONO_2$, —O-alkyl-$ONO_2$, —$OCOOR_4$, —O(C=O)-aryl, —$CHR_4OH$, —$CH_2OH$, —$CH_2O(C=O)$-aryl, —$CH_2O(C=O)$—$R_4$, —$CHR_4O$(C=O)-aryl, —$CHR_4O(C=O)$—$R_4$, unsaturated carboxylic ester, $C_2$-$C_{12}$ alkynyl, substituted $C_2$-$C_{12}$ alkynyl, —$NHSO_2R_4$, —$SR_4$, —$SO_2R_4$, —$SO_2NHR_4$, or —$SO_2NR_4R_5$, or Y and J bond together to form a carbocyclic or aromatic ring, wherein $R_4$ and $R_5$ are independently H, $C_1$-$C_6$ alkyl, $C_6$-$C_8$ aryl, substituted $C_1$-$C_6$ alkyl, substituted $C_6$-$C_8$ aryl, $C_5$-$C_{12}$ cycloalkyl, $C_7$-$C_{12}$ alkylaryl, -alkyl-$NR_6R_7$, -alkyl-$OR_6$, -alkyl-$ONO_2$, —$S(O)_{0-2}$-(alkyl-$NR_6R_7$), wherein $R_6$ and $R_7$ are independently H, alkyl, aryl or bond together with nitrogen atom to form a heterocyclic ring, and $R_1$, $R_2$ and $R_3$ are H, $C_1$-$C_6$ alkyl, cycloalkyl, aryl, alkylaryl, alkylheteroaryl, alkylheterocycle, wherein any one thereof is optionally substituted with one or more of OH, $ONO_2$, or $NR_8R_9$, wherein $R_8$ and $R_9$ are independently H, $C_1$-$C_6$ alkyl, $C_6$-$C_8$ aryl or bond together with nitrogen atom to form a heterocyclic ring.

In some embodiments, the pharmaceutically acceptable salt of the compound may comprise a salt form of such as HCl, $CH_3SO_3H$, tartaric acid, maleic acid, fumaric acid, malic acid, lactic acid or p-TSA.

In some embodiments, $R_1$, $R_2$ and $R_3$ may be $—(CH_2)_nNR_{10}R_{11}$ or $—(CH_2)_nOH$, wherein $R_{10}$ and $R_{11}$ are independently H, $C_1$-$C_6$ alkyl, $C_6$-$C_8$ aryl or bond together with nitrogen atom to form a $C_5$-$C_{10}$ heterocyclic ring, and n is an integer from 1 to 6.

In some embodiments, $R_8$ and $R_9$ may be bond together with nitrogen atom to form a $C_3$-$C_{10}$ heterocyclic ring.

In some embodiments, $R_6$ and $R_7$ may be independently H, $C_1$-$C_6$ alkyl, $C_6$-$C_8$ aryl or bond together with nitrogen atom to form a $C_5$-$C_{10}$ heterocyclic ring.

In some embodiments, the compound may be

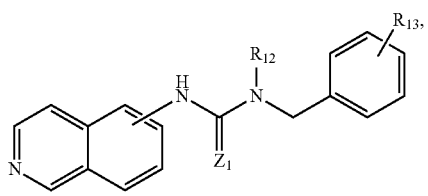

wherein $R_{13}$ is H, $C_1$-$C_6$ alkyl, $C_6$-$C_8$ aryl, $C_1$-$C_6$ aminoalkyl, $—NH_2$, $—CN$, $—OH$, $—O$-alkyl, $—O$-aryl, $—COOH$, $—COOR_{14}$, $—CONHR_{14}$, $—CONHCH_2$-aryl, $—CONR_{14}CH_2$-aryl, $—NHCOR_{14}$, halogen, $C_1$-$C_6$ halogened alkyl, -alkyl-$OR_{14}$, $—O$-alkyl-$OR_{14}$, -alkyl-$ONO_2$, O-alkyl-$ONO_2$, $—OCOOR_{14}$, $—O(C=O)$-aryl, $—CHR_{14}OH$, $—CH_2OH$, $—CH_2O(C=O)$-aryl, $—CH_2O(C=O)—R_4$, $—CHR_{14}$, $—O(C=O)$-aryl, $—CHR_4O(C=O)—R_{14}$, wherein $R_{14}$ is H, $C_1$-$C_6$ alkyl, $C_6$-$C_8$ aryl, $C_5$-$C_{12}$ cycloalkyl, $C_6$-$C_{12}$ alkylaryl, and $R_{12}$ is —H, $C_1$-$C_6$ alkyl, $—(CH_2)_nNR_{15}R_{16}$ or $—(CH_2)_nOH$, wherein $R_{15}$ and $R_{16}$ are independently H, $C_1$-$C_6$ alkyl, $C_6$-$C_8$ aryl or bond together with nitrogen atom to form a $C_5$-$C_{10}$ heterocyclic ring, and $Z_1$ is N—CN, NH, $NR_{17}$, $NCOR_{17}$, $NCONR_{17}R_{18}$, NCO-aryl, S, or O, wherein $R_{17}$ and $R_{18}$ are independently H, $C_1$-$C_6$ alkyl, $C_6$-$C_8$ aryl, substituted $C_1$-$C_6$ alkyl, substituted $C_6$-$C_8$ aryl, $C_5$-$C_{12}$ cycloalkyl, or $C_7$-$C_{12}$ alkylaryl.

In some embodiments, the compound may be

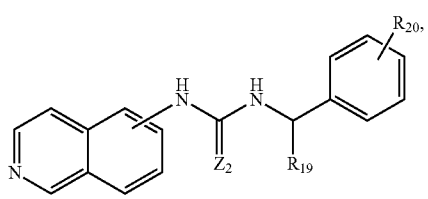

wherein $R_{20}$ is H, $C_1$-$C_6$ alkyl, $C_6$-$C_8$ aryl, $C_1$-$C_6$ aminoalkyl, $—NH_2$, $—CN$, $—OH$, $—O$-alkyl, $—O$-aryl, $—COOH$, $—COOR_{21}$, $—CONHR_{21}$, $—CONHCH_2$-aryl, $—CONR_{21}CH_2$-aryl, $—NHCOR_{21}$, halogen, $C_1$-$C_6$ halogened alkyl, -alkyl-$OR_{21}$, $—O$-alkyl-$OR_{21}$, -alkyl-$ONO_2$, O-alkyl-$ONO_2$, $—OCOOR_{21}$, $—O(C=O)$-aryl, $—CHR_{21}OH$, $—CH_2OH$, $—CH_2O(C=O)$-aryl, $—CH_2O(C=O)—R_4$, $—CHR_{21}O(C=O)$-aryl, or $—CHR_4O(C=O)—R_{21}$, wherein $R_{21}$ is H, $C_1$-$C_6$ alkyl, $C_6$-$C_8$ aryl, $C_5$-$C_{12}$ cycloalkyl, $C_6$-$C_{12}$ alkylaryl, and $R_{19}$ is —H, $C_1$-$C_6$ alkyl, $—(CH_2)_nNR_{22}R_{23}$ or $—(CH_2)_nOH$, wherein $R_{22}$ and $R_{23}$ are independently H, $C_1$-$C_6$ alkyl, $C_6$-$C_8$ aryl or bond together with nitrogen atom to form a $C_5$-$C_{10}$ heterocyclic ring, and $Z_2$ is N—CN, NH, $NR_{24}$, $NCOR_{24}$, $NCONR_{24}R_{25}$, NCO-aryl, S, or O, wherein $R_{24}$ and $R_{25}$ are independently H, $C_1$-$C_6$ alkyl, $C_6$-$C_8$ aryl, substituted $C_1$-$C_6$ alkyl, substituted $C_6$-$C_8$ aryl, $C_5$-$C_{12}$ cycloalkyl, or $C_7$-$C_{12}$ alkylaryl.

In some embodiments, the compound may be

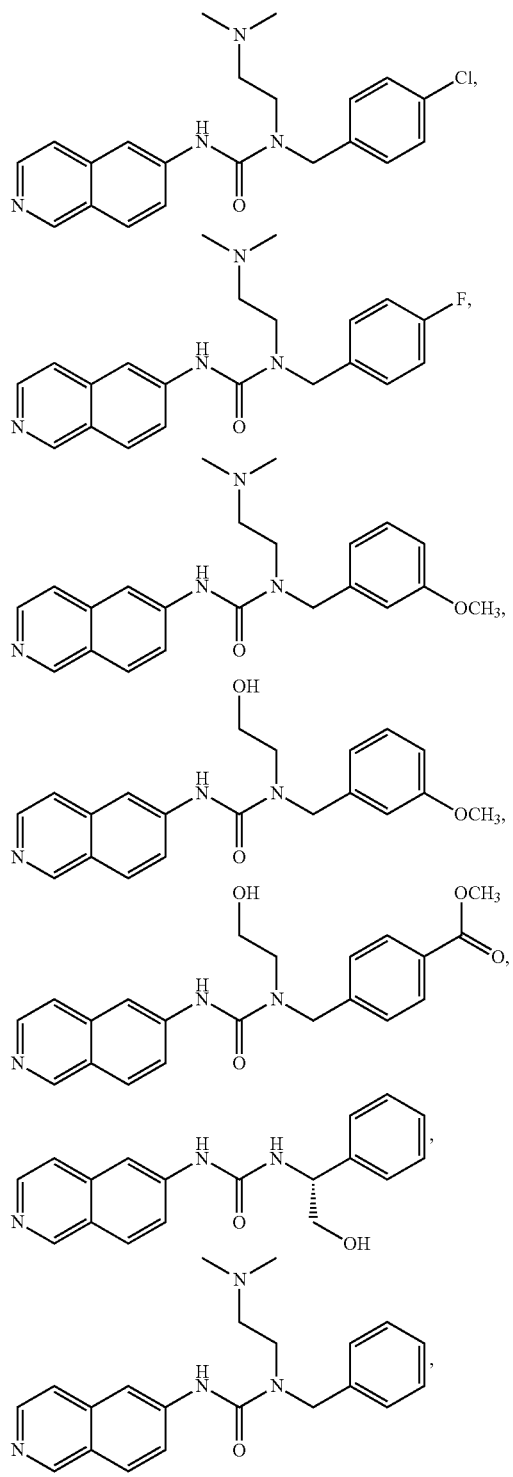

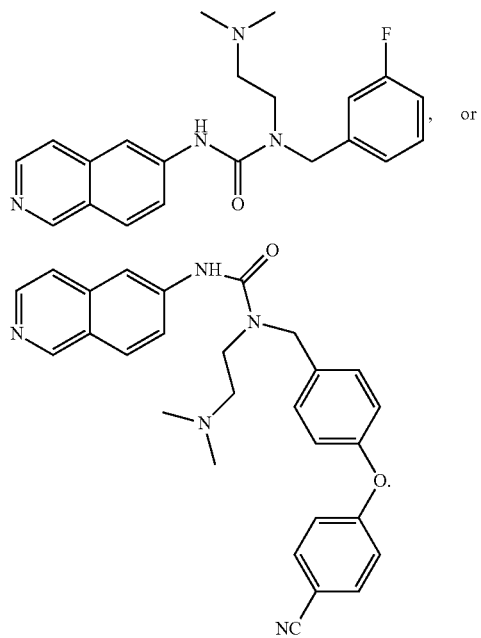
In some embodiments, the compound may comprise
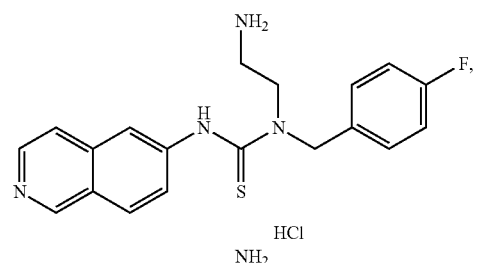
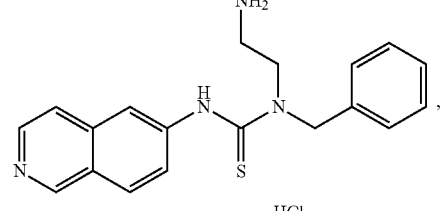
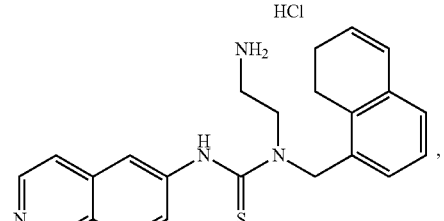
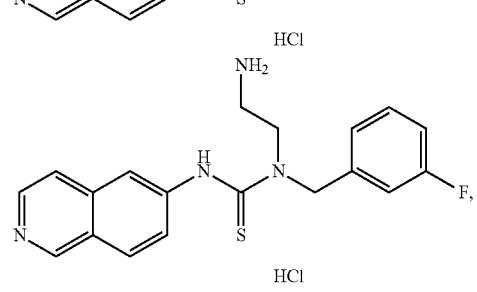
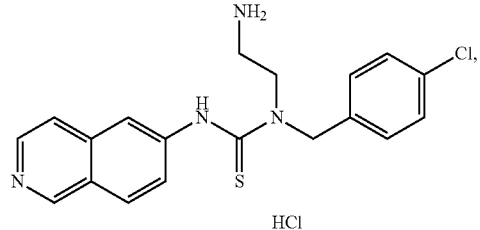
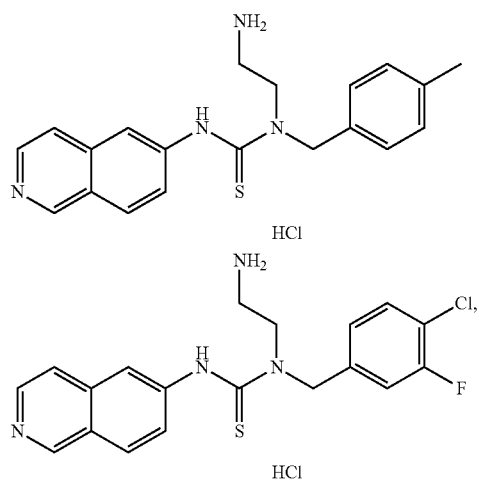
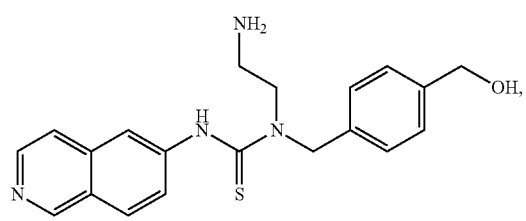
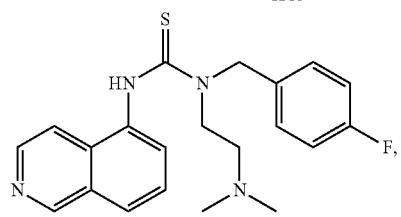

-continued

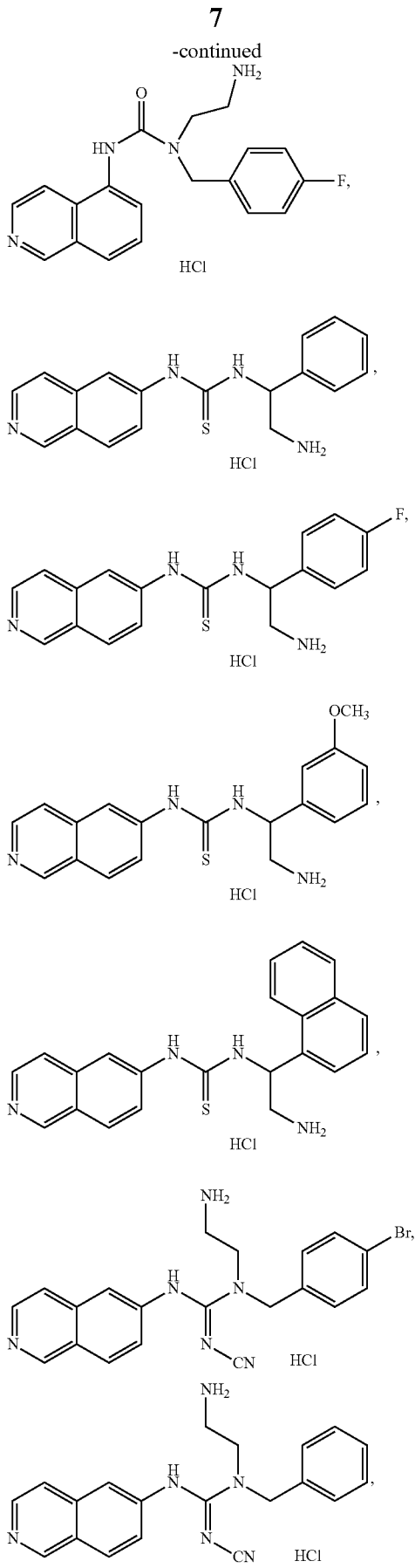

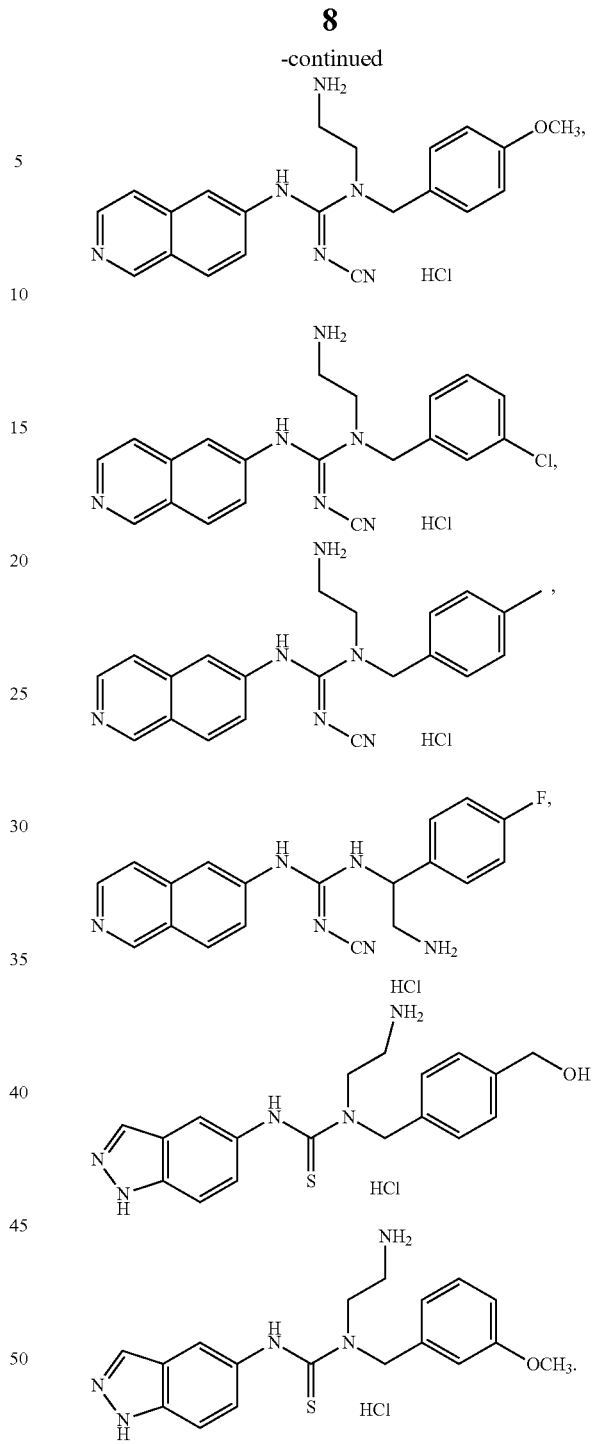

In some embodiments, the compound may comprise a prodrug, an optical isomer or a racemic mixture thereof.

In some embodiments, the compound may serve as, for example, an AGC kinase inhibitor.

In accordance with one embodiment of the disclosure, a pharmaceutical composition is provided. The pharmaceutical composition comprises an effective amount of a compound or a pharmaceutically acceptable salt thereof, and a pharmaceutically acceptable carrier.

The compound contained in the pharmaceutical composition may be represented by formula (I).

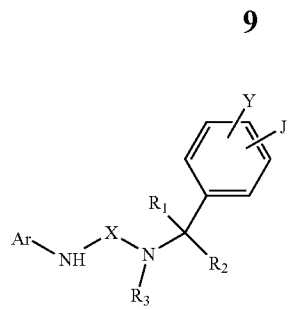

(I)

In formula (I), Ar is indazole, 5-isoquinoline, 6-isoquinoline, or their N-oxide, X is —C(=Z)—, wherein Z is N—CN, NH, $NR_4$, $NCOR_4$, $NCONR_4R_5$, NCO-aryl, S, or O, Y and J are independently H, $C_1$-$C_6$ alkyl, $C_6$-$C_8$ aryl, $C_1$-$C_6$ aminoalkyl, —$NH_2$, —CN, —OH, —O-alkyl, —O-aryl, —COOH, —$COOR_4$, —$CONHR_4$, —$CONHCH_2$-aryl, —$CONR_4CH_2$-aryl, —$NHCOR_4$, halogen, $C_1$-$C_6$ halogened alkyl, -alkyl-$OR_4$, -alkyl-$ONO_2$, —O-alkyl-$ONO_2$, —$OCOOR_4$, —O(C=O)-aryl, —$CHR_4OH$, —$CH_2OH$, —$CH_2O(C=O)$-aryl, —$CH_2O(C=O)$—$R_4$, —$CHR_4O$(C=O)-aryl, —$CHR_4O(C=O)$—$R_4$, unsaturated carboxylic ester, $C_2$-$C_{12}$ alkynyl, substituted $C_2$-$C_{12}$ alkynyl, —$NHSO_2R_4$, —$SR_4$, —$SO_2R_4$, —$SO_2NHR_4$, or —$SO_2NR_4R_5$, or Y and J bond together to form a carbocyclic or aromatic ring, wherein $R_4$ and $R_5$ are independently H, $C_1$-$C_6$ alkyl, $C_6$-$C_8$ aryl, substituted $C_1$-$C_6$ alkyl, substituted $C_6$-$C_8$ aryl, $C_5$-$C_{12}$ cycloalkyl, $C_7$-$C_{12}$ alkylaryl, -alkyl-$NR_6R_7$, -alkyl-$OR_6$, -alkyl-$ONO_2$, —$S(O)_{0-2}$-(alkyl-$NR_6R_7$), wherein $R_6$ and $R_7$ are independently H, alkyl, aryl or bond together with nitrogen atom to form a heterocyclic ring, and $R_1$, $R_2$ and $R_3$ are H, $C_1$-$C_6$ alkyl, cycloalkyl, aryl, alkylaryl, alkylheteroaryl, alkylheterocycle, wherein any one thereof is optionally substituted with one or more of OH, $ONO_2$, or $NR_8R_9$, wherein $R_8$ and $R_9$ are independently H, $C_1$-$C_6$ alkyl, $C_6$-$C_8$ aryl or bond together with nitrogen atom to form a heterocyclic ring.

In some embodiments, the pharmaceutically acceptable carrier may comprise 6-aminoisoquinoline or 5-aminoisoquinoline, or their N-oxide.

In some embodiments, the pharmaceutical composition may be an eye drop formulation.

The compound of formula (I) may be synthesized by scheme I depicted as follows.

Scheme I

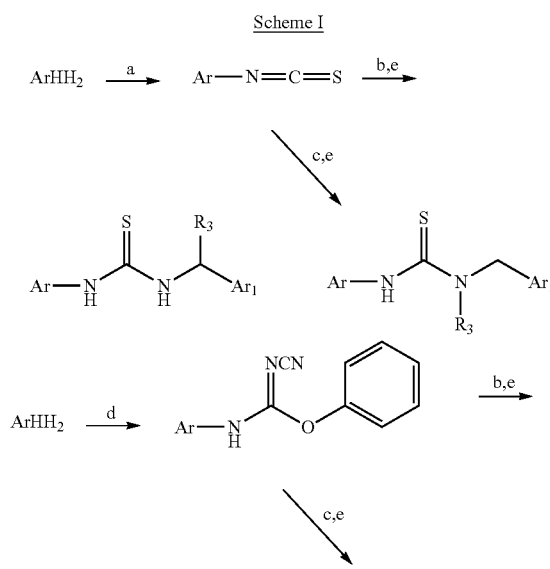

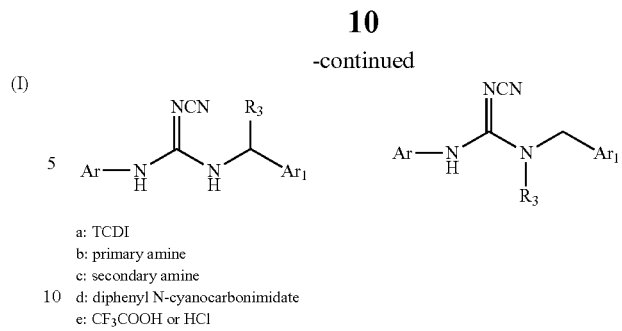

a: TCDI
b: primary amine
c: secondary amine
d: diphenyl N-cyanocarbonimidate
e: $CF_3COOH$ or HCl The intermediate compounds of formula (II) may be synthesized by scheme IIB depicted as follows.

Scheme II (A) primary amine:

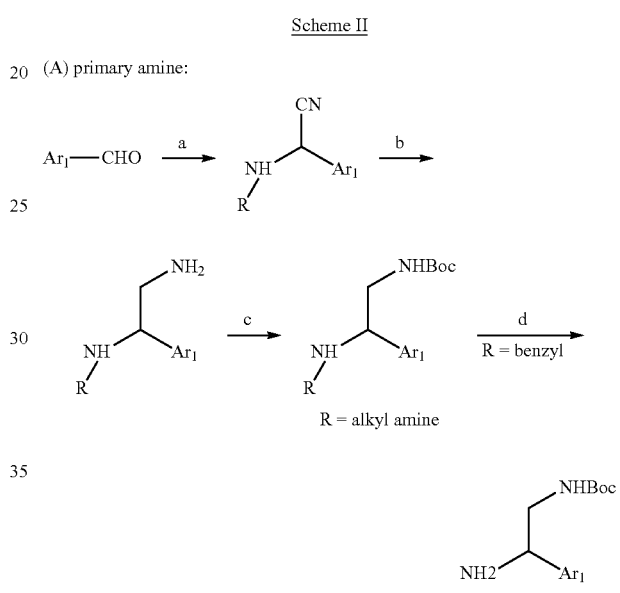

a: benzylamine or alkyl amine/KCN/HOAc
b: $LiAlH_4$
c: $(Boc)_2O/Et_3N$
d: $Pd(OH)_2/H_2$ (B) secondary amine:

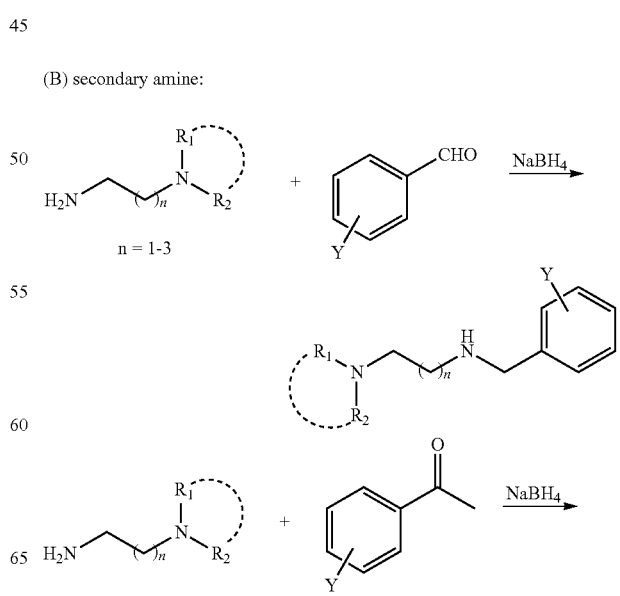

-continued

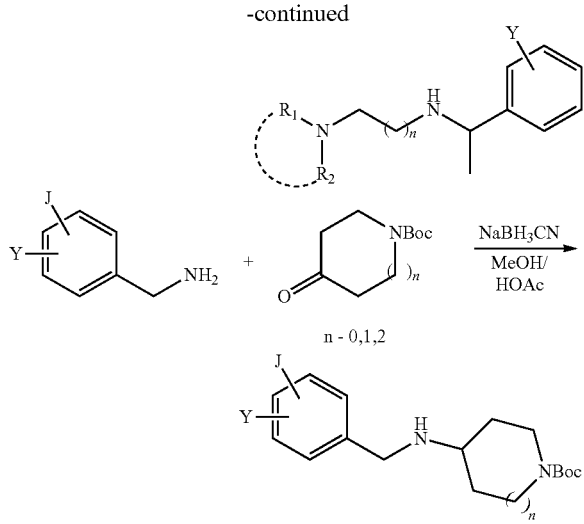

n - 0,1,2

Example 1: Preparation of 1-(2-aminoethyl)-1-(1-(4-fluorophenyl)ethyl)-3-(isoquinolin-6-yl)urea hydrochloride

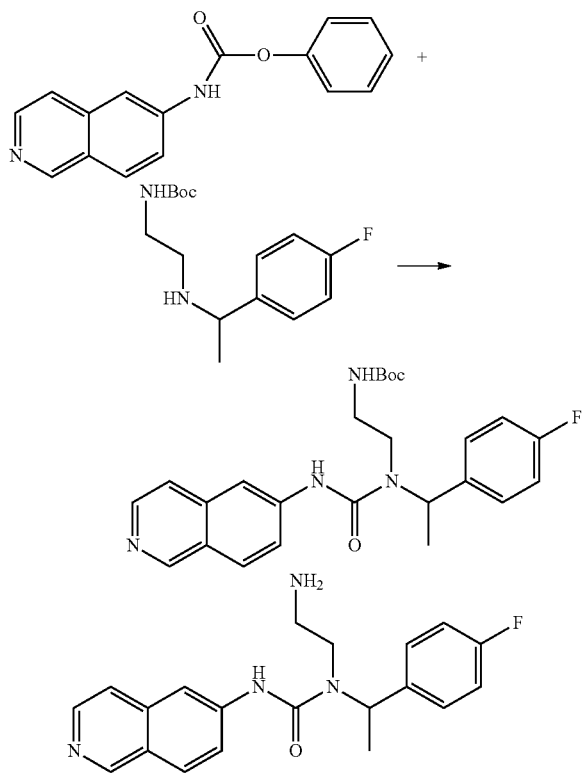

21.24 mg phenyl isoquinolin-6-ylcarbamate and 22.7 mg tert-butyl 2-(1-(4-fluorophenyl)ethylamino)ethylcarbamate in DMF were reacted at 110° C. for 1 hr. Water was added to the mixture and extracted with EA. The EA layer was thoroughly washed with water and dried by $Na_2SO_4$. After the EA layer was concentrated, the reaction intermediate was washed out by a column (EA/hexane=1:1). The reaction intermediate was then added to 1.5 ml MeOH/0.5M HCl solution with stirring overnight. After the reaction was completed, a portion of methanol was distilled off and acetone was added with stirring for 10 minutes. After filtration, 19 mg of the hydrochloride salt product was obtained.

The NMR spectral data of the compound is listed below:
$^1$H NMR (500 MHz CD3OD): δ1.71 (d, 3H), 2.14 (s, 2H), 2.84 (t, 2H), 3.45 (m, 1H), 3.54 (m, 1H), 5.62 (q, 1H), 7.16 (t, 2H), 7.47 (t, 2H), 8.22 (d, 2H), 8.39 (d, 2H), 8.56 (s, 1H), 9.50 (s, 1H).

Example 2: Preparation of 1-(2-aminoethyl)-1-(1-(4-fluorophenyl)ethyl)-3-(isoquinolin-5-yl)urea HCl The preparation method of Example 2 is similar to that provided by Example 1. The distinction therebetween is that the compound "isoquinolin-6-ylcarbamate" was replace by the compound "phenyl isoquinolin-5-ylcarbamate phenyl" to obtain the product "1-(2-aminoethyl)-1-(1-(4-fluorophenyl)ethyl)-3-(isoquinoline-5-yl)urea".

The NMR spectral data of the compound is listed below:
$^1$H NMR (500 MHz CD3OD): δ1.74 (d, 3H), 2.87 (t, 2H), 3.45 (m, 1H), 3.56 (m, 1H), 5.60 (q, 1H), 7.22 (t, 2H), 7.57 (t, 2H), 8.05 (t, 1H), 8.18 (d, 2H), 8.34 (d, 1H), 8.40 (d, 1H), 8.58 (d, 1H), 9.79 (s, 1H).

Example 3: Preparation of 1-(3,4-difluorobenzyl)-1-(2-(dimethylamino)ethyl)-3-(isoquinolin-5-yl)urea 18.7 mg phenyl isoquinolin-5-ylcarbamate and 15.2 mg N-(3,4-difluorobenzyl)-N',N'-dimethylethane-1,2-diamine in DMSO were reacted at 110° C. for 2 hr. Water was added to the mixture and extracted with EA. The EA layer was thoroughly washed with water and dried by $Na_2SO_4$. After the EA layer was concentrated, the reaction intermediate was washed out by a column (100% EA, EA/MeOH=1:1). After purification, 19.6 mg of the product was obtained.

The NMR spectral data of the compound is listed below:
$^1$H NMR (500 MHz $CDCl_3$): δ 2.42 (s, 6H), 2.65 (t, 2H), 3.49 (t, 2H), 4.59 (s, 2H), 7.10 (m, 2H), 7.15 (m, 1H), 7.57 (t, 1H), 7.68 (m, 2H), 7.91 (d, 1H), 8.48 (d, 1H), 9.21 (s, 1H), 10.30 (b, 1H).

Example 4: Preparation of 1-(2-(dimethylamino)ethyl)-3-(isoquinolin-5-yl)-1-((pyridin-4-yl)methyl)urea 38.6 mg phenyl isoquinolin-5-ylcarbamate and 26.2 mg N-((pyridin-4-yl)methyl)-N',N'-dimethylethylenediamine in DMSO were reacted at 110° C. for 2 hr. Water was added to the mixture and extracted with EA. The EA layer was thoroughly washed with water and dried by $Na_2SO_4$. After the EA layer was concentrated under reduced pressure, the reaction intermediate was washed out by a column (100% EA, EA/MeOH=1:1). The eluate was concentrated and then recrystallized by EA/hexane (1:1) to give 9.6 mg of crystalline product.

The NMR spectral data of the compound is listed below:
$^1$H NMR (500 MHz $CD_3OD$): δ 2.71 (s, 6H), 3.12 (t, 2H), 3.76 (t, 2H), 4.85 (s, 2H), 7.48 (d, 2H), 7.68 (t, 1H), 7.70 (d, 1H), 7.78 (d, 1H), 7.97 (d, 1H), 8.41 (d, 1H), 8.58 (d, 1H), 9.23 (s, 1H).

Example 5: Preparation of 1-(4-fluorobenzyl)-1-(2-(dimethylamino)ethyl)-3-(isoquinolin-5-yl)thiourea

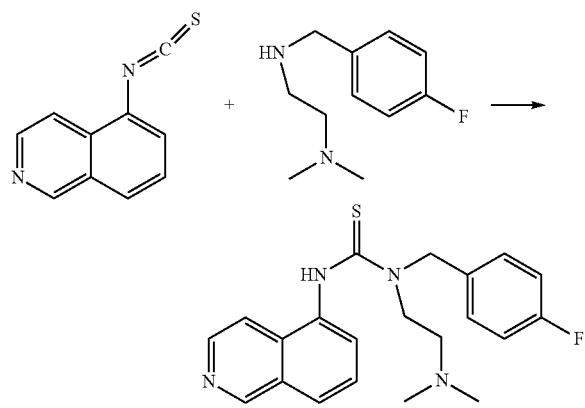

11 mg 5-isothiocyanatoisoquinoline and equivalent N-(4-fluorobenzyl)-N',N'-dimethyl-ethylenediamine in THF were reacted at room temperature overnight. Water was added to the mixture and extracted with EA. The EA layer was thoroughly washed with water and dried by $Na_2SO_4$. After purification by a silicone column (EA/MeOH=10:1), 9.6 mg of crystalline product was obtained.

The NMR spectral data of the compound is listed below:
$^1$H NMR (500 MHz $CD_3OD$): δ 2.30 (s, 6H), 2.65 (t, 2H), 3.83 (t, 2H), 5.22 (s, 2H), 7.16 (t, 2H), 7.49 (t, 2H), 7.67 (m, 3H), 8.01 (d, 1H), 8.39 (d, 1H), 9.24 (s, 1H).

Example 6: Preparation of 1-(4-fluorobenzyl)-1-(2-aminoethyl)-3-(isoquinolin-6-yl)thiourea

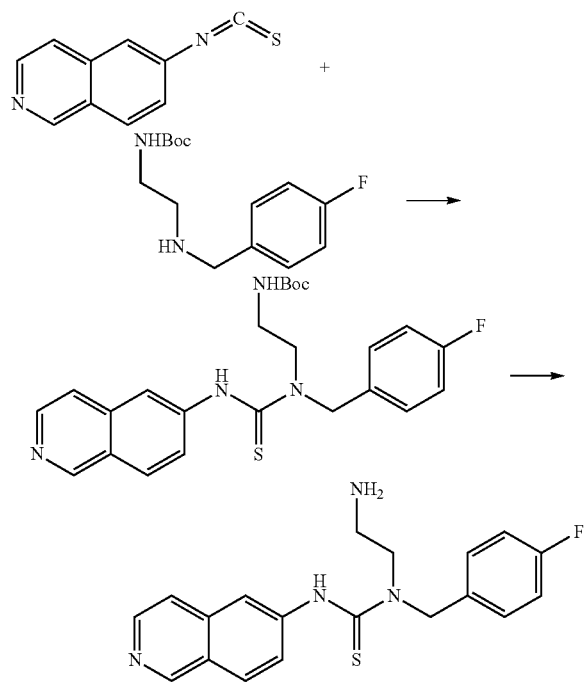

6.8 mg 6-isothiocyanatoisoquinoline and 24.2 mg tert-butyl 2-(4-fluorobenzylamino)ethylcarbamate in 1.5 ml DMF were stirred at room temperature overnight. Water was added to the mixture and extracted with EA. The EA layer was thoroughly washed with water and dried by $Na_2SO_4$. After the EA layer was concentrated under reduced pressure, the reaction intermediate "tert-butyl 2-(1-(4-fluorobenzyl)-3-(isoquinolin-6-yl)thioureido)ethylcarbamate" containing Boc was obtained. The reaction intermediate containing Boc was added to 1.5 ml 6N HCl/1 ml MeOH with stirring at room temperature overnight to obtain a solution containing suspended solid. The solid was then filtered and washed with acetone to give 16 mg of hydrochloride salt product.

The NMR spectral data of the compound is listed below:
$^1$H NMR (500 MHz DMSO d-6): δ 3.14 (t, 2H), 4.04 (t, 2H), 5.17 (s, 2H), 7.22 (t, 2H), 7.37 (m, 2H), 8.11 (m, 4H), 8.26 (d, 1H), 8.34 (d, 1H), 8.53 (d, 1H) 9.62 (s, 1H), 10.22 (s, 1H).

Example 7: Preparation of 1-(4-chloro-3-fluorobenzyl)-1-(2-aminoethyl)-3-(isoquinolin-6-yl)thiourea hydrochloride

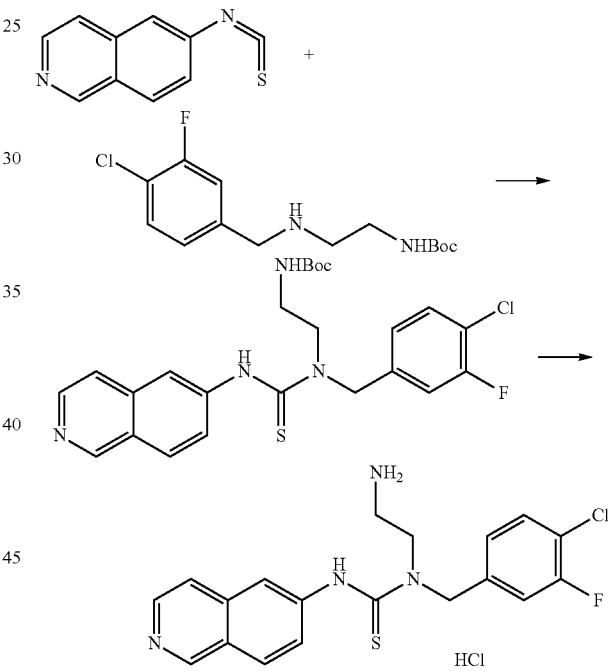

15.7 mg (84.3 mmole) 6-isothiocyanatoisoquinoline, 25.6 mg (84.5 mmole) tert-butyl-2-(4-chloro-3-fluorobenzylamino)ethylcarbamate, and 5 ml acetone were added to a reaction bottle at room temperature with stirring for 1 hour. After removing acetone by vacuum, the residue was purified by a SiO2 column (EA/Hexane=1:1). The intermediate product was added to 0.3 ml 6N HCl and reacted overnight. The reaction liquid was drained under reduced pressure and stirred with 3 ml acetone. The suspended solid was filtered and washed with acetone, and then the solid was taken and evaporated in vacuum to give 14.9 g (42%) of product.

The NMR spectral data of the compound is listed below:
$^1$H NMR (500 MHz DMSO d-6): δ 3.16 (t, 2H), 4.05 (t, 2H), 5.21 (s, 2H), 7.36 (b, 1H), 7.45 (t, 1H), 7.57 (d, 1H), 8.14 (b, 4H), 8.29 (d, 1H), 8.36 (d, 1H), 8.54 (d, 1H), 9.64 (s, 1H), 10.41 (s, 1H).

Example 8: Preparation of 1-(3-chlorobenzyl)-1-(2-aminoethyl)-3-(isoquinolin-6-yl)thiourea hydrochloride

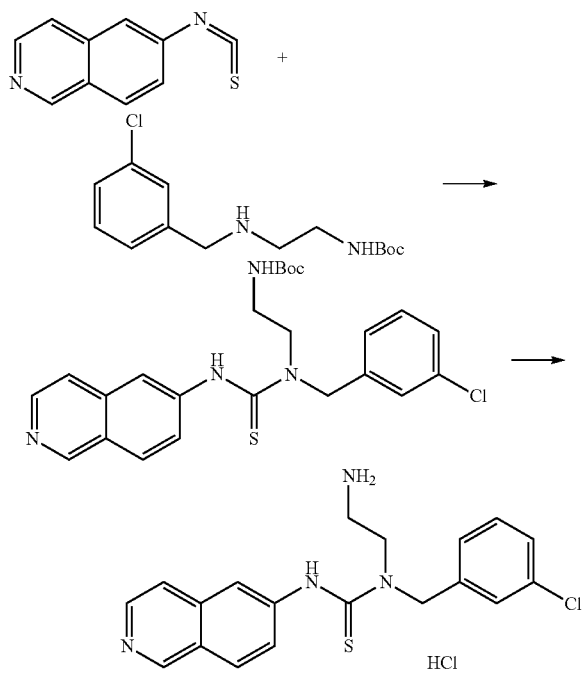

14.4 mg 6-isothiocyanatoisoquinoline, 22 mg tert-butyl-2-(3-chlorobenzylamino)ethylcarbamate, and 3 ml acetone were added to a reaction bottle at room temperature with stirring for 1 hour. After removing acetone by vacuum, the residue was purified by a SiO2 column (EA/Hexane=1:1). The intermediate product was added to 0.3 ml 6N HCl and reacted overnight. 4 ml methanol was added and filtered. The reaction liquid was drained under reduced pressure and stirred with 3 ml acetone/methanol (10:1). The suspended solid was filtered and washed with acetone, and then the solid was taken and evaporated in vacuum to give 7.9 mg of product.

The NMR spectral data of the compound is listed below:
$^1$H NMR (500 MHz DMSO d-6): δ 3.17 (t, 2H), 4.09 (t, 2H), 5.23 (s, 2H), 7.30 (d, 1H), 7.38 (m, 2H), 7.43 (m, 1H), 8.15 (b, 4H), 8.29 (d, 1H), 8.35 (d, 1H), 8.54 (d, 1H), 9.46 (s, 1H), 10.41 (s, 1H).

Example 9: Preparation of 1-(2-amino-1-(4-fluorophenyl)ethyl)-3-(isoquinolin-6-yl)urea hydrochloride

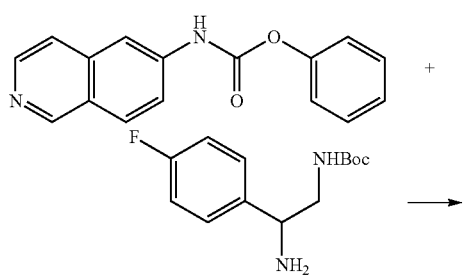

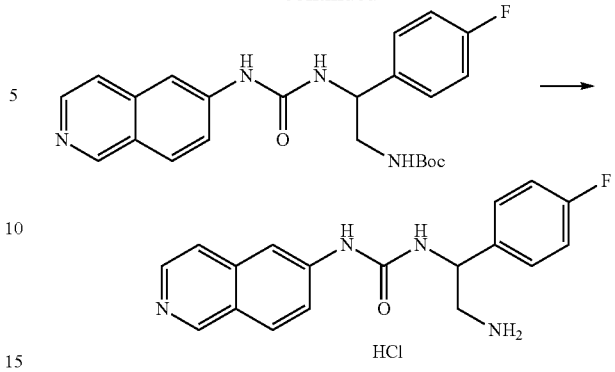

47 mg phenyl isoquinolin-6-ylcarbamate and 47.7 mg tert-butyl-2-amino-2-(4-fluorophenyl)ethylcarbamate in DMF were reacted at 110° C. for 1 hour. Water was added to the reactant and extracted with EA. The EA layer was thoroughly washed with water and dried by Na$_2$SO$_4$. After the EA layer was concentrated, solid was precipitated by EA/Hexane (1:1). The intermediate solid was added to 6N HCl solution with stirring overnight. After the reaction was completed, the mixture was evaporated to dry under reduced pressure. A small amount of methanol was added, and the mixture was stirred for 10 minutes with acetone, and filtered to give 45.6 mg of hydrochloride salt product.

The NMR spectral data of the compound is listed below:
$^1$H NMR (500 MHz CD$_3$OD): δ 3.29 (m, 1H), 3.35 (m, 1H), 5.17 (b, 1H), 7.12 (t, 2H), 7.46 (q, 2H), 7.90 (d, 1H), 8.12 (d, 1H), 8.30 (m, 4H), 8.42 (s, 1H), 9.38 (s, 1H).

Example 10: Preparation of 1-(2-amino-1-(3-methoxyphenyl)ethyl)-3-(isoquinolin-6-yl)thiourea hydrochloride

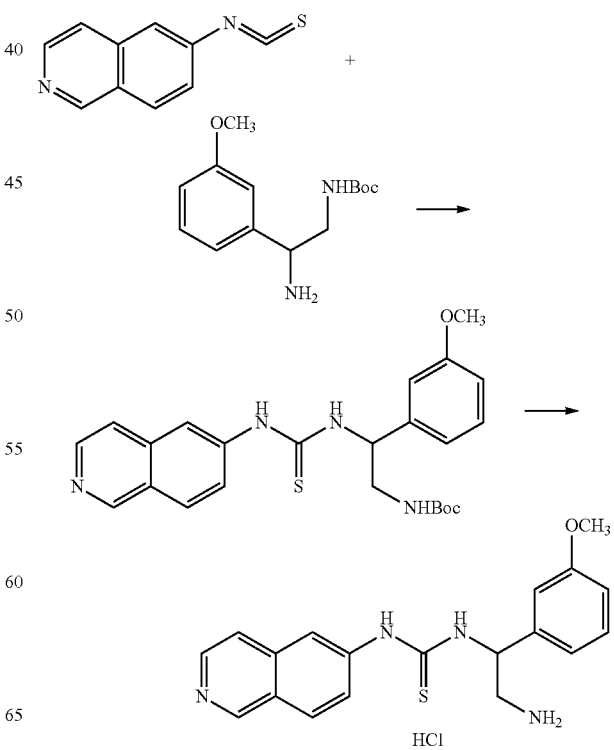

20 mg 6-isothiocyanatoisoquinoline, 33 mg tert-butyl-2-amino-2-phenylethylcarbamate, and 5 ml THF were added to a reaction bottle at room temperature with stirring overnight. After removing THF by vacuum, the residue was purified by a SiO2 column (EA/Hexane=1:1). The intermediate product was added to 6N HCl and reacted overnight. After the reaction liquid was concentrated under reduced pressure, 1.5 ml acetone/methanol (10:1) was added. The precipitate was filtered and washed with acetone, and then the solid was taken and evaporated in vacuum to give 13 mg of hydrochloride salt product.

The NMR spectral data of the compound is listed below:
$^1$H NMR (500 MHz DMSO d-6): δ 3.25 (m, 2H), 3.79 (s, 3H), 5.76 (dd, 1H), 6.90 (d, 1H), 7.03 (d, 1H), 7.08 (s, 1H), 7.31 (t, 1H), 8.09 (d, 1H), 8.19 (b, 3H), 8.25 (d, 1H), 8.37 (d, 1H), 8.49 (d, 1H), 8.76 (s, 1H), 9.59 (s, 1H), 9.72 (s, 1H), 11.4 (s, 1H), (d, 1H), 11.44 (s, 1H).

Example 11: Preparation of 1-(2-amino-1-(naphthalen-1-yl)ethyl)-3-(isoquinolin-6-yl)thiourea hydrochloride

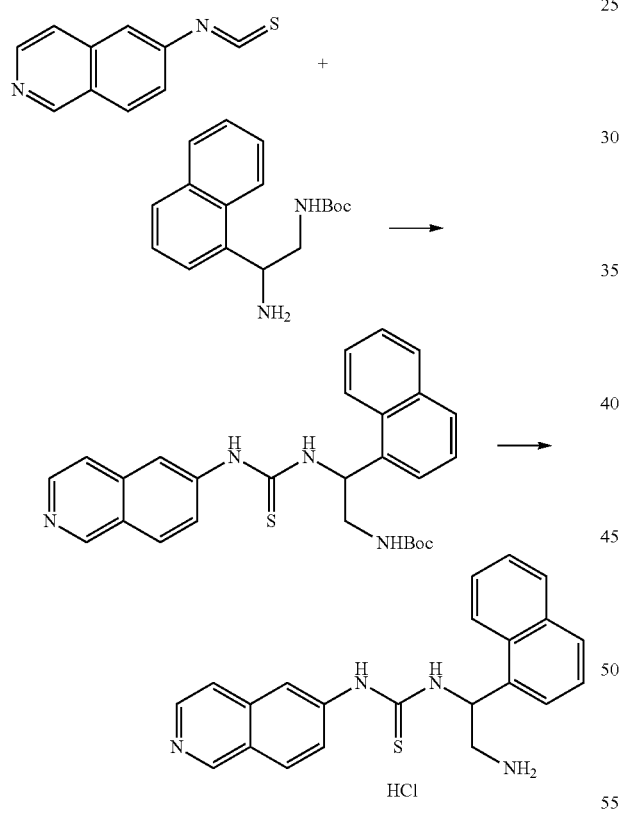

18.2 mg 6-isothiocyanatoisoquinoline, 28.1 mg tert-butyl-2-amino-2-(naphthalen-1-yl)ethylcarbamate, and 5 ml THF were added to a reaction bottle at room temperature with stirring overnight. After removing THF by vacuum, the residue was purified by a SiO2 column (EA/Hexane=1:1). The intermediate product was added to 6N HCl and reacted overnight. After the reaction liquid was concentrated under reduced pressure, 1.5 ml acetone/methanol (10:1) was added. The precipitate was filtered and washed with acetone, and then the solid was taken and evaporated in vacuum to give 12 mg of product.

Example 12: Preparation of 1-(2-amino-1-phenyl-ethyl)-3-(isoquinolin-6-yl)thiourea

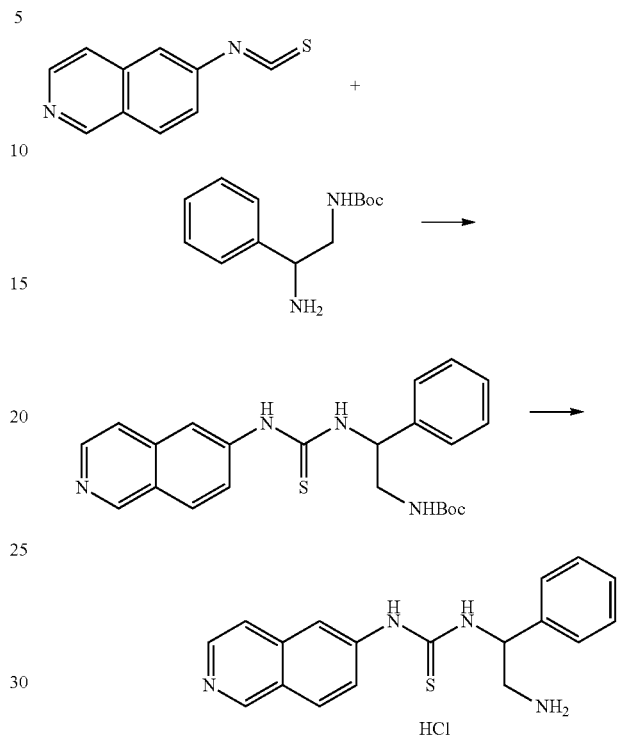

26.63 mg 6-isothiocyanatoisoquinoline, 33.8 mg tert-butyl-2-amino-2-phenylethylcarbamate, and 5 ml THF were added to a reaction bottle at room temperature with stirring overnight. After removing THF by vacuum, the residue was purified by a SiO2 column (EA/Hexane=1:1). The intermediate product was added to 0.2 ml MeOH/0.5 ml HCl (3M in ether) and reacted overnight. After filtering and washing with acetone, the solid was taken and evaporated in vacuum to give 32 mg of product.

The NMR spectral data of the compound is listed below:
$^1$H NMR (500 MHz DMSO d-6): δ 3.25 (m, 2H), 5.79 (d, d, 1H), 7.34 (t, 1H), 7.41 (t, 2H), 7.48 (d, 2H), 8.10 (d, 1H), 8.22 (b, 2H), 8.28 (d, 1H), 8.40 (d, 1H), 8.49 (d, 1H), 8.79 (s, 1H), 9.62 (s, 1H), 9.83 (d, 1H), 11.44 (s, 1H).

Example 13: Preparation of 1-(4-bromobenzyl)-1-(2-aminoethyl)-2-cyano-3-(isoquinolin-6-yl)guanidine hydrochloride

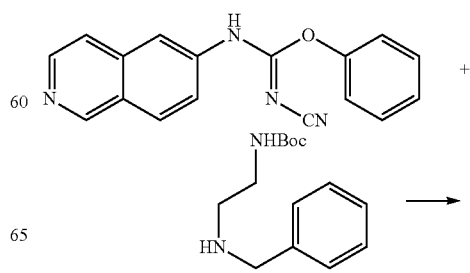

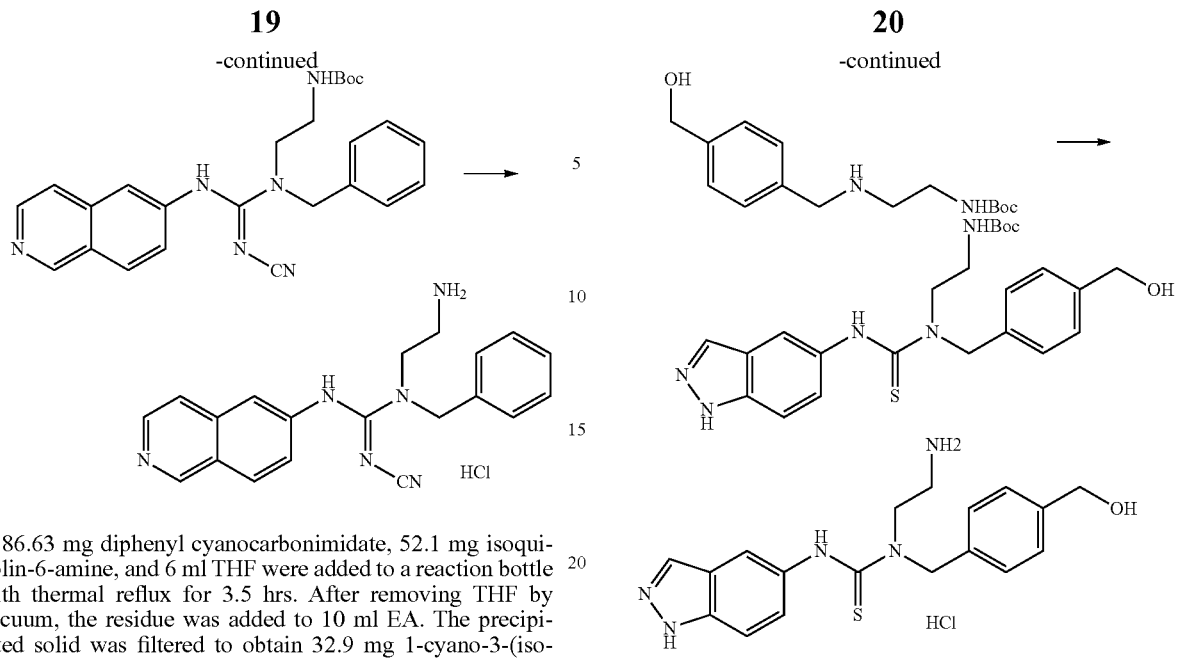

86.63 mg diphenyl cyanocarbonimidate, 52.1 mg isoquinolin-6-amine, and 6 ml THF were added to a reaction bottle with thermal reflux for 3.5 hrs. After removing THF by vacuum, the residue was added to 10 ml EA. The precipitated solid was filtered to obtain 32.9 mg 1-cyano-3-(isoquinolin-6-yl)-2-phenylisourea. The intermediate was reacted with equivalent tert-butyl-2-(benzylamino)ethylcarbamate and 20 mg of DIPEA in 5 ml DMF at 110° C. for 18 hrs. After cooling, 1N NaOH was added and extracted twice with EA. After the combined EA layer was dried and concentrated by Na$_2$SO$_4$, 26.4 mg intermediate product was eluted out by a SiO2 column (EA/Hexane 4:1). The intermediate was added to 1.5 ml 6N HCl at room temperature with stirring overnight. After the reaction solution was evaporated under reduced pressure, 2 ml acetone/methanol (10:1) was added. The precipitate was filtered and washed with acetone, and then the solid was taken and evaporated in vacuum to give 18.7 mg of product.

Example 14: Preparation of 1-(4-methoxybenzyl)-1-(2-aminoethyl)-2-cyano-3-(isoquinolin-6-yl)guanidine hydrochloride The preparation is similar to Example 13. Tert-butyl-2-(benzylamino)ethylcarbamate was replaced by tert-butyl-2-(4-methoxybenzylamino)ethylcarbamate.
The NMR spectral data of the compound is listed below:
$^1$H NMR (500 MHz DMSO d-6): δ 3.12 (m, 2H), 3.71 (s, 3H), 3.78 (m, 2H), 5.02 (b, 2H), 6.90 (d, 1H), 7.32 (b, 1H), 8.21 (b, 3H), 8.68 (d, 1H), 8.73 (d, 1H), 9.56 (s, 1H).

Example 15: Preparation of 1-(3-chlorobenzyl)-1-(2-aminoethyl)-2-cyano-3-(isoquinolin-6-yl)guanidine hydrochloride The preparation is similar to Example 13. Tert-butyl-2-(benzylamino)ethylcarbamate was replaced by tert-butyl 2-(3-chlorobenzylamino)ethylcarbamate.

Example 16: Preparation of 1-(4-fluorobenzyl)-1-(2-aminoethyl)-3-(1H-indazol-5-yl)thiourea hydrochloride

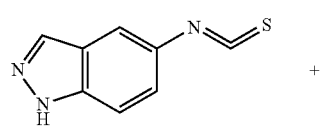

+

19.7 mg 5-isothiocyanato-1H-indazole, 31.2 mg tert-butyl 2-(4-(hydroxymethyl)benzylamino)ethylcarbamate and 5 ml acetone were added in a reaction bottle and reacted at room temperature overnight. After removing acetone under reduced pressure and purifying by a SiO2 column (EA/Hexane=2:1), an intermediate product was obtained. The intermediate product was added to a mixing solution of 0.7 ml 3M HCl/ether and 0.1 ml MeOH and stirred overnight at room temperature. The precipitated solid was filtered and the crystalline solid was washed with acetone. The solid was evaporated to dryness to yield 9.5 mg of product.

Example 17: Preparation of 6-isothiocyanatoisoquinoline Intermediate 1.81 g isoquinolin-6-amine, 2.46 g TCDI and 2 eq Et3N in 8 ml THF were stirred at room temperature for 4 hours. After removing THF by vacuum, the residue was purified by a column (EA/Hexane=1:1) to give 1.06 g of product.
The NMR spectral data of the compound is listed below:
$^1$H NMR (500 MHz DMSO d-6): δ 7.67 (d, 1H), 7.81 (d, 1H), 8.04 (s, 1H), 8.21 (d, 1H), 8.54 (d, 1H), 9.33 (s, 1H).

Example 18: Preparation of Phenyl isoquinolin-6-ylcarbamate Intermediate

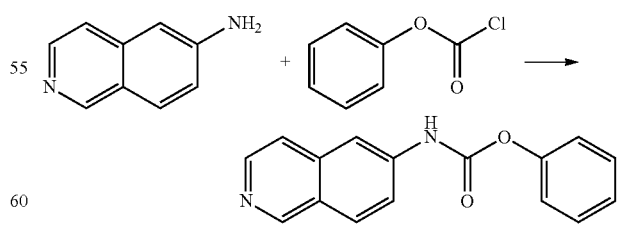

3.46 g 6-amino isoquinoline was added in 32 ml THF and stirred in a water bath at room temperature. 4.03 g (1.3 eq) DIPEA was then added. At this time, 4.1344 g phenylchloroformate was slowly added to the stirred reaction solution. After about 30 minutes, the reaction was heated and refluxed for 1 hour. After removing THF by vacuum, the residue was purified by a SiO2 column (EA/Hexane=1:1) to give 3.06 g of solid product (yield: 48.2%).

The NMR spectral data of the compound is listed below:
$^1$H NMR (500 MHz DMSO d-6): δ 7.24 (m, 3H), 7.44 (t, 2H), 7.72 (d, d, 2H), 8.03 (d, 1H), 8.12 (s, 1H), 8.40 (d, 1H), 9.16 (d, 1H), 10.69 (s, 1H).

To measure Rho-kinase inhibition, $IC_{50}$ values were determined according to the following ELISA protocol:

ROCK Substrate Coated Plate (Part No 241601): One strip well 96-well plate pre-coated with recombinant MYPT1.

Buffer: 25 mM Tris, pH 7.5, 10 mM $MgCl_2$, 5 mM Glycerol-2-Phosphate, 0.1 mM $Na_3VO_4$; 1% DMSO; 2.5 mM DTT; (Enzyme: ROCK active-II) (Cell Biolabs, Catalog #STA-406, Part No. 241505) 0.1 ng/μl.

ATP Solution (Part No. 241604): 100 mM ATP. Final concentration of ATP in reaction mixture: 250 μM.

Anti-phospho-MYPT1 (Thr696) (Part No. 241603).

Secondary Antibody, HRP Conjugate (Part No. 231003).

Biotinylated substrate, diluted to 0.25 μM with buffer described above (without ATP).

Steps:

1. Purified kinase or cell lysate sample can be used directly in the kinase assay or further diluted with 1× Kinase Buffer. Each sample should be assayed in duplicate.

2. Add 90 μL of the diluted active ROCK-II positive control or unknown ROCK samples to the wells of the substrate plate.

3. Initiate the kinase reaction by adding 10 μL of the 10× Kinase Reaction Buffer containing DTT and ATP. Mix well.

4. Cover with a plate cover and incubate the wells at 30° C. for 30-60 minutes with gentle agitation.

5. Stop kinase reaction by flicking out the content or by adding 50 μL of 0.5M EDTA, pH 8.0, to each well.

6. Remove the plate cover and empty wells. Wash microwell strips 3 times with 250 μL 1× Wash Buffer per well with thorough aspiration between each wash. After the last wash, empty wells and tap microwell strips on absorbent pad or paper towel to remove excess 1× Wash Buffer.

7. Add 100 μL of the diluted anti-phospho-MYPT1 (Thr696) antibody to each well.

8. Cover with the plate cover and incubate at room temperature for 1 hour on an orbital shaker.

9. Remove the plate cover and empty wells. Wash the strip wells 3 times according to step 6 above.

10. Add 100 μL of the diluted HRP-conjugated secondary antibody to each well.

11. Cover with the plate cover and incubate at room temperature for 1 hour on an orbital shaker.

12. Remove the plate cover and empty wells. Wash microwell strips 3 times according to step 6 above. Proceed immediately to the next step.

13. Warm Substrate Solution to room temperature. Add 100 μL of Substrate Solution to each well, including the blank wells. Incubate at room temperature for 5-20 minutes on an orbital shaker.

14. Stop the enzyme reaction by adding 100 μL of Stop Solution into each well, including the blank wells. Results should be read immediately (color will fade over time).

15. Read absorbance of each microwell on a spectrophotometer using 450 nm as the primary wave length.

The given activity (shown in Table 1 and Table 2) is denoted as the negative logarithm of the $IC_{50}$ ($pIC_{50}$) as follows:

+: $pIC_{50} < 6.0$
++: $6.0 < pIC_{50} < 7.0$
+++: $7.0 < pIC_{50} < 8.0$
++++: $pIC_{50} > 8.0$

TABLE 1

| formula (I) | structure | ROCK2 $IC_{50}$ |
|---|---|---|
| 1 | N-(isoquinolin-6-yl)-N'-(2-(dimethylamino)ethyl)-N'-(4-chlorobenzyl)urea | +++ |
| 2 | N-(isoquinolin-6-yl)-N'-(2-(dimethylamino)ethyl)-N'-(4-fluorobenzyl)urea | +++ |
| 3 | N-(isoquinolin-6-yl)-N'-(2-(dimethylamino)ethyl)-N'-(3-methoxybenzyl)urea | ++ |

TABLE 1-continued

| formula (I) | structure | ROCK2 IC$_{50}$ |
|---|---|---|
| 4 | isoquinolin-6-yl NH-C(O)-N(CH$_2$CH$_2$OH)-CH$_2$-(3-methoxyphenyl) | ++ |
| 5 | isoquinolin-6-yl NH-C(O)-N(CH$_2$CH$_2$OH)-CH$_2$-(4-methoxycarbonylphenyl) | + |
| 6 | isoquinolin-6-yl NH-C(O)-NH-CH(phenyl)-CH$_2$OH | +++ |
| 7 | isoquinolin-6-yl NH-C(O)-N(CH$_2$CH$_2$N(CH$_3$)$_2$)-CH$_2$-phenyl | + |
| 8 | isoquinolin-6-yl NH-C(O)-N(CH$_2$CH$_2$N(CH$_3$)$_2$)-CH$_2$-(3-fluorophenyl) | ++ |
| 9 | isoquinolin-6-yl NH-C(O)-N(CH$_2$CH$_2$N(CH$_3$)$_2$)-CH$_2$-(4-(4-cyanophenoxy)phenyl) | + |

TABLE 2

| formula (I) | structure | ROCK IC$_{50}$ |
|---|---|---|
| 1 | isoquinolin-6-yl urea with N-(2-(dimethylamino)ethyl)-N-(4-fluorobenzyl) | + |
| 2 | isoquinolin-6-yl urea with N-(2-hydroxyethyl)-N-(3-methoxybenzyl) | + |
| 3 | isoquinolin-6-yl urea with (S)-2-hydroxy-1-phenylethyl | + |
| 4 | isoquinolin-5-yl urea with (S)-2-hydroxy-1-phenylethyl | + |
| 5 | isoquinolin-5-yl urea with N-(2-(dimethylamino)ethyl)-N-(4-fluorobenzyl) | + |
| 6 | isoquinolin-5-yl urea with N-(2-(dimethylamino)ethyl)-N-benzyl | ++ |

TABLE 2-continued

| formula (I) | structure | ROCK IC$_{50}$ |
|---|---|---|
| 7 | *N-(isoquinolin-5-yl)-N'-(2-(dimethylamino)ethyl)-N'-(4-chlorobenzyl)urea* | ++ |
| 8 | *N-(isoquinolin-6-yl)-N'-(2-aminoethyl)-N'-(4-fluorobenzyl)urea* | ++ |
| 9 | *N-(isoquinolin-5-yl)-N'-(4-chlorobenzyl)-N'-(piperidin-4-yl)urea* | + |
| 10 | *N-(isoquinolin-5-yl)-N'-(2-(dimethylamino)ethyl)-N'-(4-(methoxycarbonyl)benzyl)urea* | + |
| 11 | *N-(isoquinolin-5-yl)-N'-(2-(dimethylamino)ethyl)-N'-(4-fluorobenzyl)thiourea* | ++ |
| 12 | *N-(isoquinolin-5-yl)-N'-(2-(dimethylamino)ethyl)-N'-(4-(hydroxymethyl)benzyl)thiourea* | + |

TABLE 2-continued
| formula (I) | structure | ROCK IC$_{50}$ |
|---|---|---|
| 13 | 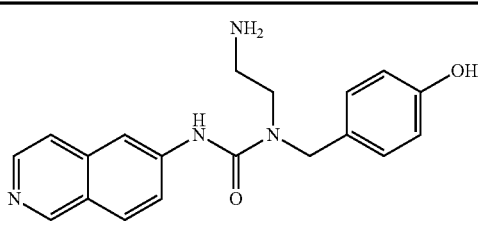 | + |
| 14 | 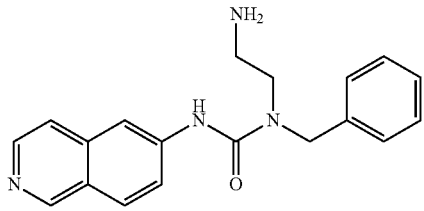 | ++ |
| 15 | 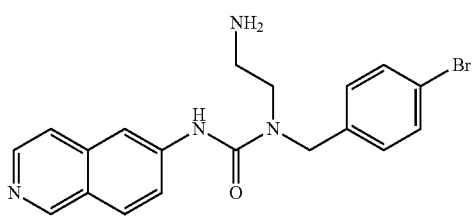 [SMILES: NCCN(Cc1ccc(Br)cc1)C(=O)Nc1ccc2cnccc2c1] | ++ |
| 16 | 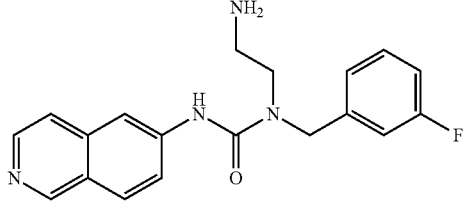 [SMILES: NCCN(Cc1cccc(F)c1)C(=O)Nc1ccc2cnccc2c1] | ++ |
| 17 | 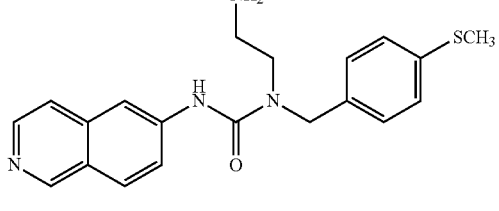 | + |
| 18 | 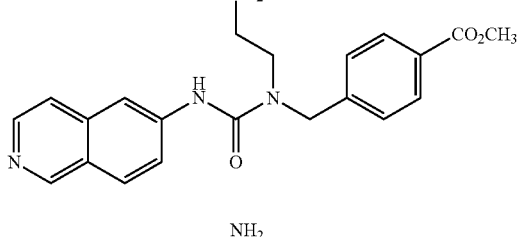 | + |
| 19 | 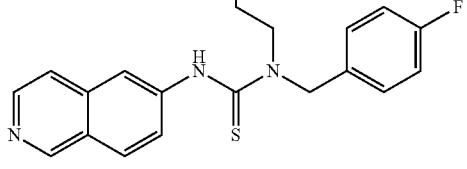 | ++ |

TABLE 2-continued
| formula (I) | structure | ROCK IC$_{50}$ |
|---|---|---|
| 20 | 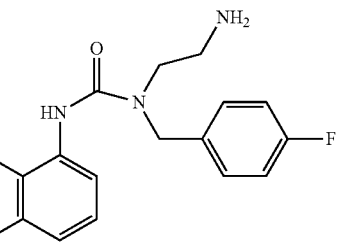 | + |
| 21 | 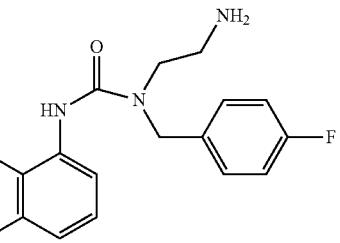 | + |
| 22 | 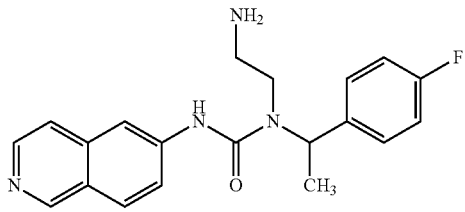 | ++ |
| 23 | 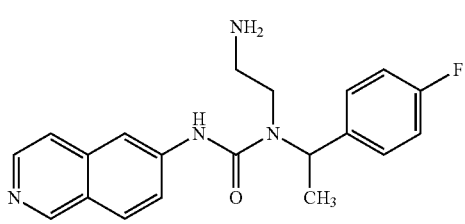 [SMILES: CC(c1ccc(F)cc1)N(CCN)C(=O)Nc1ccc2cnccc2c1] | +++ |
| 24 | 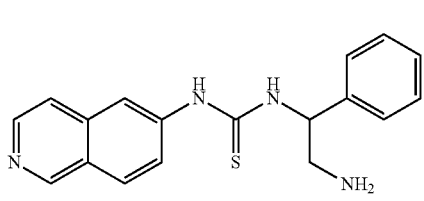 [SMILES: NCC(NC(=S)Nc1ccc2cnccc2c1)c1ccccc1] | ++++ |
| 25 | 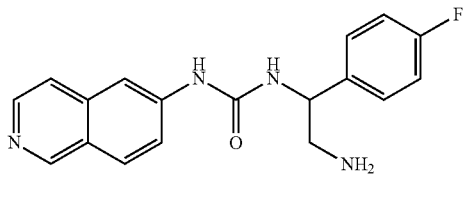 [SMILES: NCC(NC(=O)Nc1ccc2cnccc2c1)c1ccc(F)cc1] | ++++ |
| 26 | 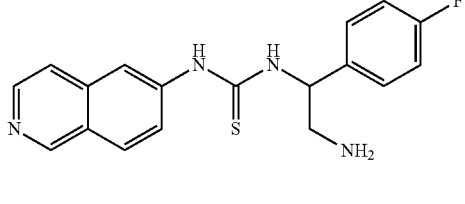 | ++++ |

TABLE 2-continued
| formula (I) | structure | ROCK IC$_{50}$ |
|---|---|---|
| 27 | 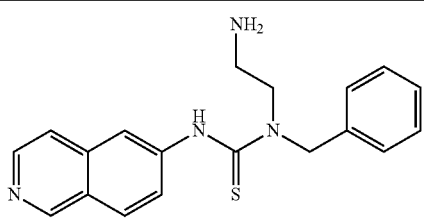 | ++ |
| 28 | 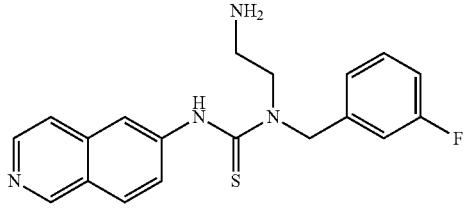 | ++ |
| 29 | 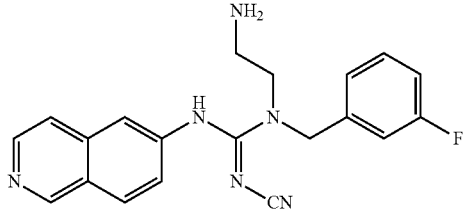 [SMILES: N#C/N=C(/Nc1ccc2cnccc2c1)N(CCN)Cc1cccc(F)c1] | +++ |
| 30 | 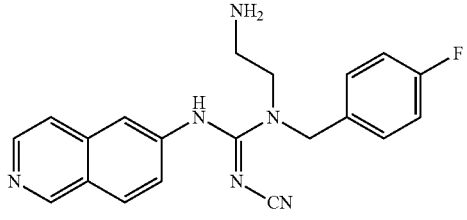 [SMILES: N#C/N=C(/Nc1ccc2cnccc2c1)N(CCN)Cc1ccc(F)cc1] | +++ |
| 31 | 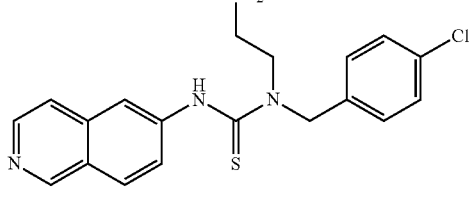 | ++++ |
| 32 | 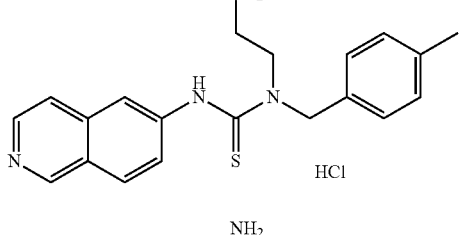 | ++ |
| 33 | 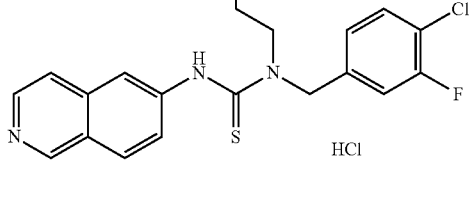 | ++ |

TABLE 2-continued

| formula (I) | structure | ROCK IC$_{50}$ |
|---|---|---|
| 34 | isoquinolin-6-yl-NH-C(=N-CN)-N(CH$_2$CH$_2$NH$_2$)(CH$_2$-C$_6$H$_4$-4-Br) | +++ |
| 35 | isoquinolin-6-yl-NH-C(=S)-NH-CH(3-methoxyphenyl)-CH$_2$NH$_2$ | ++++ |
| 36 | isoquinolin-6-yl-NH-C(=N-CN)-N(CH$_2$CH$_2$NH$_2$)(CH$_2$-C$_6$H$_5$) | ++++ |
| 37 | isoquinolin-6-yl-NH-C(=N-CN)-N(CH$_2$CH$_2$NH$_2$)(CH$_2$-C$_6$H$_4$-4-OCH$_3$) | ++++ |
| 38 | isoquinolin-6-yl-NH-C(=S)-N(CH$_2$CH$_2$NH$_2$)(CH$_2$-C$_6$H$_4$-3-Cl) | +++ |
| 39 | isoquinolin-6-yl-NH-C(=S)-NH-CH(naphth-1-yl)-CH$_2$NH$_2$ · HCl | ++++ |

What is claimed is:

1. A compound of formula (I), or a pharmaceutically acceptable salt thereof:

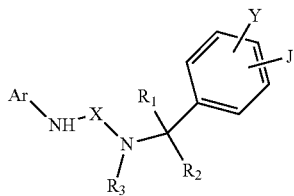

(I)

wherein Ar is, 5-isoquinoline, 6-isoquinoline, or their N-oxide,

X is —C(=Z)—, wherein Z is N—CN, NH, NR$_4$, NCOR$_4$, NCONR$_4$R$_5$, NCO-aryl, or S, Y and J are independently H, C$_1$-C$_6$ alkyl, C$_6$-C$_8$ aryl, C$_1$-C$_6$ aminoalkyl, —NH$_2$, —CN, —OH, —O-alkyl, —O-aryl, —COOH, —COOR$_4$, —CONHR$_4$, —CONHCH$_2$-aryl, —CONR$_4$CH$_2$-aryl, —NHCOR$_4$, halogen, C$_1$-C$_6$ halogened alkyl, -alkyl-OR$_4$, —O-alkyl-OR$_4$, -alkyl-ONO$_2$, —O-alkyl-ONO$_2$, —OCOOR$_4$, —O(C=O)-aryl, —CHR$_4$OH, —CH$_2$OH, —CH$_2$O(C=O)-aryl, —CH$_2$O(C=O)—R$_4$, —CHR$_4$O(C=O)-aryl, —CHR$_4$O(C=O)—R$_4$, unsaturated carboxylic ester, C$_2$-C$_{12}$ alkynyl, substituted C$_2$-C$_{12}$ alkynyl, —NHSO$_2$R$_4$, —SR$_4$, —SO$_2$R$_4$, —SO$_2$NHR$_4$, or —SO$_2$NR$_4$R$_5$, wherein R$_4$ and R$_5$ are independently H, C$_1$-C$_6$ alkyl, C$_6$-C$_8$ aryl, substituted C$_1$-C$_6$ alkyl, substituted C$_6$-C$_8$ aryl, C$_5$-C$_{12}$ cycloalkyl, C$_7$-C$_{12}$ alkylaryl, -alkyl-NR$_6$R$_7$, -alkyl-OR$_6$, -alkyl-ONO$_2$, —S(O)$_{0-2}$-(alkyl-NR$_6$R$_7$), wherein R$_6$ and R$_7$ are independently H, alkyl, aryl or bond together with nitrogen atom to form a heterocyclic ring, and R$_1$, R$_2$ and R$_3$ are H, C$_1$-C$_6$ alkyl, cycloalkyl, aryl, alkylaryl, alkylheteroaryl, alkylheterocycle, wherein any one thereof is optionally substituted with one or more of OH, ONO$_2$, or NR$_8$R$_9$, wherein R$_8$ and R$_9$ are independently H, C$_1$-C$_6$ alkyl, C$_6$-C$_8$ aryl or bond together with nitrogen atom to form a heterocyclic ring.

2. The compound as claimed in claim 1, wherein the pharmaceutically acceptable salt of the compound comprises a salt form of HCl, CH$_3$SO$_3$H, tartaric acid, maleic acid, fumaric acid, malic acid or lactic acid.

3. The compound as claimed in claim 1, wherein the compound comprises a prodrug, an optical isomer or a racemic mixture thereof.

4. The compound as claimed in claim 1, wherein R$_1$, R$_2$ and R$_3$ are —(CH$_2$)$_n$NR$_{10}$R$_{11}$ or —(CH$_2$)$_n$OH, wherein R$_{10}$ and R$_{11}$ are independently H, C$_1$-C$_6$ alkyl, C$_6$-C$_8$ aryl or bond together with nitrogen atom to form a C$_5$-C$_{10}$ heterocyclic ring, and n is an integer from 1 to 6.

5. The compound as claimed in claim 1, wherein R$_8$ and R$_9$ bond together with nitrogen atom to form a C$_3$-C$_{10}$ heterocyclic ring.

6. The compound as claimed in claim 1, wherein R$_6$ and R$_7$ are independently H, C$_1$-C$_6$ alkyl, C$_6$-C$_8$ aryl or bond together with nitrogen atom to form a C$_5$-C$_{10}$ heterocyclic ring.

7. The compound as claimed in claim 1, wherein the compound is

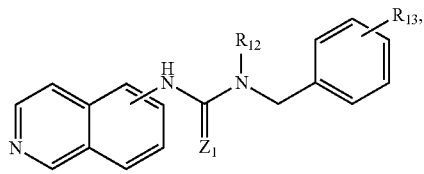

wherein R$_{13}$ is H, C$_1$-C$_6$ alkyl, C$_6$-C$_8$ aryl, C$_1$-C$_6$ aminoalkyl, —NH$_2$, —CN, —OH, —O-alkyl, —O-aryl, —COOH, —COOR$_{14}$, —CONHR$_{14}$, —CONHCH$_2$-aryl, —CONR$_{14}$CH$_2$-aryl, —NHCOR$_{14}$, halogen, C$_1$-C$_6$ halogened alkyl, -alkyl-OR$_{14}$, —O-alkyl-OR$_{14}$, O-alkyl-ONO$_2$, O-alkyl-ONO$_2$, OCOOR$_{14}$, —O(C=O)-aryl, —CHR$_{14}$OH, —CH$_2$OH, —CH$_2$O(C=O)-aryl, —CH$_2$O(C=O)—R$_4$, —CHR$_{14}$O(C=O)-aryl, —CHR$_{14}$O(C=O)—R$_{14}$, wherein R$_{14}$ is H, C$_1$-C$_6$ alkyl, C$_6$-C$_8$ aryl, C$_5$-C$_{12}$ cycloalkyl, C$_6$-C$_{12}$ alkylaryl, and R$_{12}$ is —H, C$_1$-C$_6$ alkyl, —(CH$_2$)$_n$NR$_{15}$R$_{16}$ or —(CH$_2$)$_n$OH, wherein R$_{15}$ and R$_{16}$ are independently H, C$_1$-C$_6$ alkyl, C$_6$-C$_8$ aryl or bond together with nitrogen atom to form a C$_5$-C$_{10}$ heterocyclic ring, and Z$_1$ is N—CN, NH, NR$_{17}$, NCOR$_{17}$, NCONR$_{17}$R$_{18}$, NCO-aryl, S, or O, wherein R$_{17}$ and R$_{18}$ are independently H, C$_1$-C$_6$ alkyl, C$_6$-C$_8$ aryl, substituted C$_1$-C$_6$ alkyl, substituted C$_6$-C$_8$ aryl, C$_5$-C$_{12}$ cycloalkyl, or C$_7$-C$_{12}$ alkylaryl.

8. The compound as claimed in claim 1, wherein the compound is

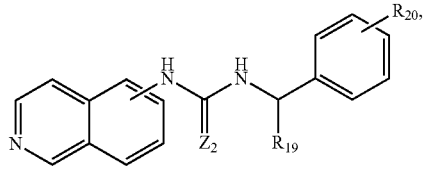

wherein R$_{20}$ is H, C$_1$-C$_6$ alkyl, C$_6$-C$_8$ aryl, C$_1$-C$_6$ aminoalkyl, —NH$_2$, —CN, —OH, —O-alkyl, —O-aryl, —COOH, —COOR$_{21}$, —CONHR$_{21}$, —CONHCH$_2$-aryl, —CONR$_{21}$CH$_2$-aryl, —NHCOR$_{21}$, halogen, C$_1$-C$_6$ halogened alkyl, -alkyl-OR$_{21}$, —O-alkyl-OR$_{21}$, -alkyl-ONO$_2$, O-alkyl-ONO$_2$, —OCOOR$_{21}$, —O(C=O)-aryl, —CHR$_{21}$OH, —CH$_2$OH, —CH$_2$O(C=O)-aryl, —CH$_2$O(C=O)—R$_4$, —CHR$_{21}$O(C=O)-aryl, —CHR$_4$O(C=O)—R$_{21}$, wherein R$_{21}$ is H, C$_1$-C$_6$ alkyl, C$_6$-C$_8$ aryl, C$_5$-C$_{12}$ cycloalkyl, C$_6$-C$_{12}$ alkylaryl, and R$_{19}$ is —H, C$_1$-C$_6$ alkyl, —(CH$_2$)$_n$NR$_{22}$R$_{23}$ or —(CH$_2$)$_n$OH, wherein R$_{22}$ and R$_{23}$ are independently H, C$_1$-C$_6$ alkyl, C$_6$-C$_8$ aryl or bond together with nitrogen atom to form a C$_5$-C$_{10}$ heterocyclic ring, and Z$_2$ is N—CN, NH, NR$_{24}$, NCOR$_{24}$, NCONR$_{24}$R$_{25}$, NCO-aryl, S, or O, wherein R$_{24}$ and R$_{25}$ are independently H, C$_1$-C$_6$ alkyl, C$_6$-C$_8$ aryl, substituted C$_1$-C$_6$ alkyl, substituted C$_6$-C$_8$ aryl, C$_5$-C$_{12}$ cycloalkyl, C$_7$-C$_{12}$ alkylaryl.

* * * * *